US006861545B2

(12) United States Patent
Citron

(10) Patent No.: US 6,861,545 B2
(45) Date of Patent: Mar. 1, 2005

(54) MANUFACTURE OF TRIALKYLALUMINUM COMPOUNDS AND α-ALCOHOLS

(75) Inventor: Joel David Citron, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 45 days.

(21) Appl. No.: 10/494,060

(22) PCT Filed: Dec. 12, 2002

(86) PCT No.: PCT/US02/39635

§ 371 (c)(1),
(2), (4) Date: Apr. 28, 2004

(87) PCT Pub. No.: WO03/053888

PCT Pub. Date: Jul. 3, 2003

(65) Prior Publication Data

US 2004/0210072 A1 Oct. 21, 2004

Related U.S. Application Data

(60) Provisional application No. 60/340,443, filed on Dec. 12, 2001.

(51) Int. Cl.$^7$ ............................. C07F 5/06; C07C 27/00
(52) U.S. Cl. ....................... 556/187; 556/190; 568/840; 568/911; 568/922
(58) Field of Search .................................. 556/187, 190; 568/840, 911, 922

(56) References Cited

U.S. PATENT DOCUMENTS

| | | | |
|---|---|---|---|
| 2,959,607 A | 11/1960 | Werber et al. | |
| 3,180,881 A | 4/1965 | Zosel et al. | |
| 3,207,770 A | 9/1965 | Zieglet et al. | |
| 3,388,143 A | 6/1968 | Rose | |
| 3,389,161 A | 6/1968 | Kottong et al. | |
| 3,474,122 A | 10/1969 | Ichiki et al. | |
| 3,487,097 A | 12/1969 | Davis | |
| 3,494,948 A | 2/1970 | Ichiki et al. | |
| 3,644,564 A | 2/1972 | van Zwet et al. | |
| 3,775,456 A | 11/1973 | Acciarri et al. | |
| 3,829,520 A | 8/1974 | Ferrell | |
| 4,689,437 A | 8/1987 | Murray | |
| 4,918,254 A | 4/1990 | Diefenbach et al. | |
| 5,210,338 A | 5/1993 | Samsel | |
| 5,276,220 A | 1/1994 | Samsel et al. | |
| 5,278,330 A | 1/1994 | Lin et al. | |
| 5,382,738 A | 1/1995 | Reagen et al. | |
| 5,430,165 A | 7/1995 | Cox et al. | |
| 5,536,859 A | 7/1996 | Lin et al. | |
| 6,103,946 A | 8/2000 | Brookhart, III et al. | |

OTHER PUBLICATIONS

J. I. Kroschwitz, et al., Ed., Encyclopedia of Chemical Technology, 4th Ed., vol. 1, John Wiley & Sons, New York, 1991, p. 834–903.
B. Elvers, et al., Ed., Ullmann's Encycolpedia of Industrial Chemistry, 5th Ed., vol. A28, 1996, p. 505–508.
W. Gerhartz, et al., Ed., Ullmann's Encyclopedia of Industrial Chemistry, 5th Ed., vol. A1, VCH Verlagsgesellschaft mbH, Weinheim, 1985, p. 545–549.
PCT/US02/39635 International Search Report dated Jun. 16, 2003.

Primary Examiner—Porfirio Nazario-Gonzalez

(57) ABSTRACT

Higher trialkylaluminum compounds may be made by forming α-olefin by oligomerizing ethylene using a transition metal containing catalyst, reacting the α-olefins formed with a lower trialkylaluminum compound to form higher trialkylaluminum compound(s) These may optionally be oxidized, as with oxygen, to form higher trialkoxyaluminum compound, which in turn may be hydrolyzed to α-alcohols. In one variation of the process lower α-olefins and higher (relatively) α-alcohols may be formed and isolated. Higher trialkylaluminum compounds and α-alcohols are useful as chemical intermediates, while lower α-olefins are useful as monomers for polyolefins.

7 Claims, No Drawings

MANUFACTURE OF TRIALKYLALUMINUM COMPOUNDS AND α-ALCOHOLS

This application claims the benefit of Provisional Application No. 60/340,443, filed Dec. 12, 2001.

FIELD OF THE INVENTION

α-Olefins are manufactured by oligomerizing ethylene using a transition metal containing catalyst, the α-olefins are converted to higher trialkylaluminum compounds by contacting the α-olefins with a lower trialkylaluminum compound usually with heating. The higher trialkylaluminum compounds which are formed may be reacted with oxygen to form the corresponding trialkoxyaluminum compounds, which can be hydrolyzed to form α-alcohols.

TECHNICAL BACKGROUND

Higher trialkylaluminum compounds (HTAC), $R^{30}{}_3Al$ (I), in which the alkyl groups contain more than 4 carbon atoms, are useful particularly as chemical intermediates for the synthesis of α-alcohols of the formula $R^{32}R^{33}CHCH_2OH$ (II) wherein $R^{32}$ is hydrogen or alkyl and $R^{33}$ is alkyl. α-Alcohols containing 10 to 20 carbon atoms are useful as intermediates for the synthesis of detergents and other surfactants. Therefore improved methods of making (I) and/or (II) are commercial interest.

Generally speaking, linear α-alcohols are often made utilizing the following steps, see for instance B. Elvers, et al., Ed., Ullmann's Encyclopedia of Industrial Chemistry, 5$^{th}$ Ed., Vol. A28, 1996, p. 505–508 and references therein, and J. I. Kroschwitz, et al., Ed, Encyclopedia of Chemical Technology, 4$^{th}$ Ed., Vol. 1, John Wiley & Sons, New York, p. 894–903 and references therein, both of which are hereby included by reference.

(a) Triethylaluminum is produced by contacting under relatively high pressure and temperature a mixture of aluminum, hydrogen, ethylene and triethylaluminum (TEA). "New" TEA is produced in the reactor. The liquid product is removed from the reactor, filtered and some is recycled back to the TEA reactor and some is used in the next step.

(b) The TEA used in the next step is now mixed with more ethylene under high pressure and with heating. The ethylene adds sequentially (oligomerizes) to each of the original ethyl groups in the TEA, forming HTACs.

(c) The product of the previous step is mixed with oxygen (a highly exothermic reaction) to form the corresponding trialkoxyaluminum compounds.

(d) The trialkoxyaluminum compounds are hydrolyzed to form an alpha-alcohol mixture and alumina.

This process is effective but requires the use of high temperatures and pressures in two steps, and in these two steps pyrophoric alkylaluminum compounds are present, and so these steps must be done very carefully to protect the plant and workers safety. This adds to the cost of the overall process. Processes which would minimize such steps, and/or require less capital investment, and/or have lower operating costs, would therefore be favored.

U.S. Pat. No. 3,207,770 and W. Gerhartz, et al., Ed., Ullmann's Encyclopedia of Industrial Chemistry, 5$^{th}$ Ed., Vol. A1, VCH Verlagsgesellschaft mbH, Weinheim, 1985, p. 545–549, describe the reaction of lower trialkylaluminum compounds (LTAC) with (usually) higher olefins. The use of higher olefins made with transition metal containing ethylene oligomerization catalysts is not mentioned.

U.S. Pat. Nos. 6,103,946, 4,689,437, 3,644,564 and 5,382,738, which are all hereby included by reference, describe the use of various transition metal containing catalysts to make olefins or mixtures of olefins by oligomerizing ethylene. No mention is made of making trialkylaluminum compounds or α-alcohols from those trialkylaluminum compounds.

B. Elvers, et al., Ed., Ullmann's Encyclopedia of Industrial Chemistry, 5$^{th}$ Ed., Vol. A28, VCH Verlagsgesellschaft mbH, Weinheim, 1996, p. 505–508 and references therein, describe the overall commercial synthesis processes for making α-alcohols, including the synthesis processes for making HTACs.

U.S. Pat. Nos. 2,959,607, 3,180,881, 3,389,161, 3,474,122, 3,494,948, 4,918,254 and 5,278,330 describe a process for the production of higher alkylaluminum compounds from (relatively) lower alkylaluminum compounds and one or more higher olefins. The use of a transition metal containing ethylene oligomerization catalyst to form olefins is not described. U.S. Pat. Nos. 2,959,607 and 5,278,330 also describe the steps of oxidation of trialkylaluminums and the hydrolysis of the resulting trialkoxyaluminum compounds.

SUMMARY OF THE INVENTION

This invention concerns, a process for the manufacture of higher trialkylaluminum compounds, comprising, forming an α-olefin or mixture of o-olefins by oligomerization of ethylene using a transition metal containing oligomerization catalyst system, then contacting said α-olefin or said mixture of α-olefins with a lower trialkylaluminum compound at a sufficient temperature, for a sufficient amount of time, to form a higher trialkylaluminum compound.

This invention also concerns a process for the manufacture of α-alcohols, comprising:

(1) forming an α-olefin or mixture of α-olefins by oligomerization of ethylene using a transition metal containing oligomerization catalyst system;

(2) contacting said α-olefin or said mixture of α-olefins with a lower trialkylaluminum compound at a sufficient temperature, for a sufficient amount of time, to form a higher trialkylaluminum compound or a mixture thereof;

(3) contacting said higher trialkylaluminum compound or a mixture thereof with oxygen or other suitable oxidizing agent to form a higher trialkoxyaluminum compound or a mixture thereof; and (4) hydrolyzing said higher trialkoxyaluminum compound or a mixture thereof to form an α-alcohol or a mixture thereof.

DETAILS OF THE INVENTION

Herein certain terms are used, and some of them are defined below:

By a "lower trialkylaluminum compound" (LTAC) is meant a compound of the formula $R^{36}{}_3Al$ (VI), in which each of $R^{36}$ contains 6 or fewer carbon atoms, preferably 2–4 carbon atoms, and each $R^{36}$ is independently alkyl. It is to be understood that the LTAC may contain impurities such as hydrogen bound to aluminum. Preferred LTACs are triethylaluminum and tri-i-butylaluminum.

By a "higher trialkylaluminum compound" (HTAC) is meant a compound of the formula $R^{31}{}_3Al$ (I), in which each of $R^{31}$ contains 6 or more carbon atoms, preferably 8 or more carbon atoms, each $R^1$ is Independently $R^{32}R^{33}CHCH_2$— wherein $R^{32}$ is hydrogen or alkyl, R33 is alkyl, and each $R^{31}$ contains an even number of carbon atoms. Preferably R³² is hydrogen and/or R33 is n-alkyl. It is to be understood that the HTAC may contain impurities such as hydrogen bound to aluminum or alkyl groups having less than 4 carbon atoms bound to aluminum, but at least 50 mole percent, more preferably at least 75 mole percent, and especially preferably at least 90 mole percent of the groups bound to aluminum are R³¹—.

By a "higher trialkoxyaluminum compound" (HTAC) is meant a compound of the formula (R³¹O)₃Al (III), in which each of R³¹ contains 4 or more carbon atoms, preferably 6 or more carbon atoms, each R³¹ is independently R³²R33CHCH₂— wherein R³² is hydrogen or alkyl, R³³ is alkyl, and each R³¹ contains an even number of carbon atoms. Preferably R³² is hydrogen and/or R³³ is n-alkyl. It is to be understood that the higher trialkoxyaluminum compound(s) may contain impurities such as alkoxy groups having less than 4 carbon atoms bound to aluminum, but at least 50 mole percent, more preferably at least 75 mole percent, and especially preferably at least 90 mole percent of the groups bound to aluminum are R³¹O—.

By an α-alcohol is meant a compound of the formula R³²R³³CHCH₂OH (II), wherein R³² is hydrogen or alkyl, R³³ is alkyl, and (II) contains an even number of carbon atoms. Preferably R³² is hydrogen and/or R³³ is n-alkyl.

By a transition metal containing ethylene oligomerizaton catalyst is meant a catalyst system which contains an element of Groups 3–12 (IUPAC notation) in the catalyst system, and which Is capable of oligomerizing ethylene to an α-olefin. Transition metal containing "inert" supports are not considered part of the catalyst system. By "inert" in this context is meant that the support is believed to function merely as a physical support and does not actually take part chemically in the oligomerization process.

By an "α-olefin" is meant a compound of the formula H₂C=CR³²R³³ (IV) wherein R³² is hydrogen or alkyl, R³³ is alkyl, and (IV) contains an even number of carbon atoms. It is preferred than R³² is hydrogen and/or R³³ is n-alkyl.

Transition metal containing catalysts that oligomerize ethylene to α-olefins may be divided into two classes, those that produce a mbdure of c-olefins and those that produce (mostly) a single α-olefin. The former are exemplified by those catalysts found in U.S. Pat. Nos. 6,103,946, 2,787,626, 3,032,574, 3,207,770, 3,644,564, 3,647,915 and 3,647,915, all of which are hereby included by reference. These oligomerizations herein may be run under conditions described in these references and in other references for other such types of catalysts. Typically these catalysts produce a homologous series of α-olefins that differ by two carbon atoms. The amounts of each olefin in the homologous series typically follow a so called Schulz-Flory distribution, which uses a factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, which is hereby included by reference). This is defined as:

K=n(C$_{n+2}$ olefin)/n(C$_n$ olefin)

wherein n(C$_n$ olefin) is the number of moles of olefin containing n carbon atoms, and n(C$_{n+2}$ olefin) is the number of moles of olefin containing n+2 carbon atoms, or in other words the next higher oligomer of C$_n$ olefin. From this can be determined the weight (mass) fractions of the various olefins in the resulting oligomeric reaction product mixture. The K factor is preferred to be in the range of about 0.6 to about 0.8

A preferred type of ethylene oligomerization catalyst is described in U.S. Pat. No. 6,103,946 and World Patent Applications 01/58874, 00/42123, 00/76659 and 01/19513, all of which are hereby included by reference, and similar iron tridentate catalysts which result in the formation of α-olefins. These catalysts utilize selected diimines of 2,6-diacylpyridines or 2,6-pyridinedicarboxaldehydes as part of the ethylene oligomerization catalyst system, particularly as iron complexes.

Such a preferred active ethylene oligomerization catalyst comprises an iron complex of a compound of the formula

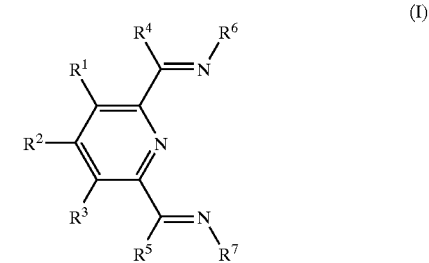

wherein:
R¹, R² and R³ are each independently hydrogen, hydrocarbyl, substituted hydrocarbyl or an inert functional group, provided that any two of R¹, R² and R³ vicinal to one another taken together may form a ring;

R⁴ and R⁵ are each independently hydrogen, hydrocarbyl, substituted hydrocarbyl or an inert functional group;

R⁶ and R⁷ are each independently a substituted aryl having a first ring atom bound to the imino nitrogen, provided that:

in R⁶, a second ring atom adjacent to said first ring atom is bound to a halogen, a primary carbon group, a secondary carbon group or a tertiary carbon group; and further provided that in R⁶, when said second ring atom is bound to a halogen or a primary carbon group, none, one or two of the other ring atoms in R⁶ and R⁷ adjacent to said first ring atom are bound to a halogen or a primary carbon group, with the remainder of the ring atoms adjacent to said first ring atom being bound to a hydrogen atom; or in R⁶, when said second ring atom is bound to a secondary carbon group, none, one or two of the other ring atoms in R⁶ and R⁷ adjacent to said first ring atom are bound to a halogen, a primary carbon group or a secondary carbon group, with the remainder of the ring atoms adjacent to said first ring atom being bound to a hydrogen atom; or in R⁶, when said second ring atom is bound to a tertiary carbon group, none or one of the other ring atoms in R⁶ and R⁷ adjacent to said first ring atom are bound to a tertiary carbon group, with the remainder of the ring atoms adjacent to said first ring atom being bound to a hydrogen atom.

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the oligomerization process or operation of the oligomerization catalyst, system. If not otherwise stated, it is preferred that substituted hydrocarbyl groups herein contain 1 to about 30 carbon atoms. Included in the meaning of "substituted" are rings containing one or more heteroatoms, such as nitrogen, oxygen and/or sulfur. In a substituted hydrocarbyl, all of the hydrogens may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include halo (fluoro, chloro, bromo and iodo), and ether such as —OR$^{50}$ wherein R$^{50}$ is hydrocarbyl or substituted hydrocarbyl. In cases in which the functional group may be near a transition metal atom, the functional group alone should not coordinate to the metal atom more strongly than the groups in those compounds that are shown as coordinating to the metal atom, that is they should not displace the desired coordinating group.

By a "primary carbon group" herein is meant a group of the formula —CH$_2$ - - -, wherein the free valence - - - is to any other atom, and the bond represented by the solid line is to a ring atom of a substituted aryl to which the primary carbon group is attached. Thus the free valence - - - may be bonded to a hydrogen atom, a halogen atom, a carbon atom, an oxygen atom, a sulfur atom, etc. In other words, the free valence - - - may be to hydrogen, hydrocarbyl, substituted hydrocarbyl or a functional group. Examples of primary carbon groups include —CH$_3$, —CH$_2$CH(CH$_3$)$_2$, —CH$_2$Cl, —CH$_2$C$_6$H$_5$, —OCH$_3$ and —CH$_2$OCH$_3$.

By a secondary carbon group is meant the group

wherein the bond represented by the solid line is to a ring atom of a substituted aryl to which the secondary carbon group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —CH(CH$_3$)$_2$, —CHCl$_2$, —CH(C$_6$H$_5$)$_2$, cyclohexyl, —CH(CH$_3$)OCH$_3$, and —CH=CCH$_3$.

By a "tertiary carbon group" is meant a group of the formula

wherein the bond represented by the solid line is to a ring atom of a substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tetiary carbon groups include —C(CH$_3$)$_3$, —C(C$_6$H$_5$)$_3$, —CC$_3$, —CF$_3$, —C(CH$_3$)OCH$_3$, —C≡CH, —C(CH$_3$)$_2$CH=CH$_2$, aryl and substituted aryl such as phenyl and 1-adamantyl.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl".

Similar to an aryl, a substituted aryl may have one or more aromatic rings which may be fused, connected by single bonds or other groups; however, is when the substituted aryl has a heteroaromatic ring, the free valence in the substituted aryl group can be to a heteroatom (such as nitrogen) of the heteroaromatic ring instead of a carbon.

By a "first ring atom in R$^6$ and R$^7$ bound to an imino nitrogen atom" is meant the ring atom in these groups bound to an imino nitrogen shown in (I), for example

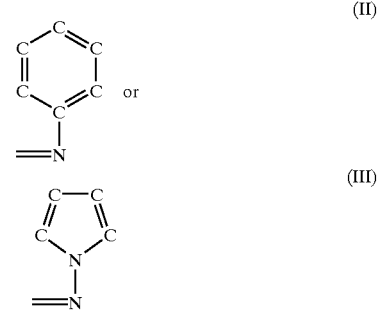

the atoms shown in the 1-position in the rings in (II) and (III) are the first ring atoms bound to an imino carbon atom (other groups which may be substituted on the aryl groups are not shown). Ring atoms adjacent to the first ring atoms are shown, for example, in (IV) and (V), where the open valencies to these adjacent atoms are shown by dashed lines (the 2,6-positions in (IV) and the 2,6positions in (V)).

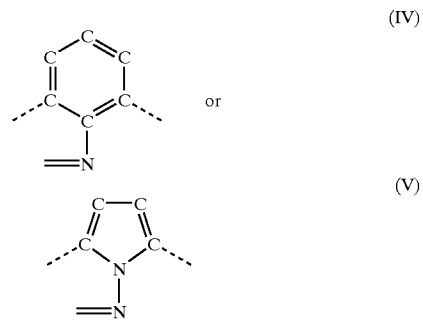

In one preferred embodiment of (I), R$^6$ is

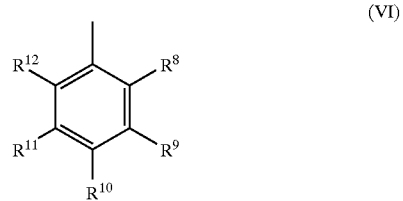

and $R^7$ is

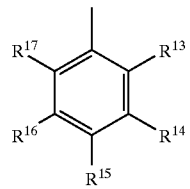

(VII)

wherein:

$R^8$ is a halogen, a primary carbon group, a secondary carbon group or a tertiary carbon group; and $R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; provided that:

when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or when $R^8$ is a tertiary carbon group, none or one of $R^{12}$, $R^{13}$ and $R^{17}$ is tertiary carbon group, with the remainder of $R^{12}$, $R^{13}$ and $R^{17}$ being hydrogen;

and further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

In the above formulas (VI) and (VII), $R^8$ corresponds to the second ring atom adjacent to the first ring atom bound to the imino nitrogen, and $R^{12}$, $R^{13}$ and $R^{17}$ correspond to the other ring atoms adjacent to the first ring atom.

In compounds (I) containing (VI) and (VII), it is particularly preferred that:

if $R^8$ is a primary carbon group, $R^{13}$ is a primary carbon group, and $R^{12}$ and $R^{17}$ are hydrogen; or if $R^8$ is a secondary carbon group, $R^{13}$ is a primary carbon group or a secondary carbon group, more preferably a secondary carbon group, and $R^{12}$ and $R^{17}$ are hydrogen; or if $R^8$ is a tertiary carbon group (more preferably a trihalo tertiary carbon group such as a trihalomethyl), $R^{13}$ is a tertiary carbon group (more preferably a trihalotertiary group such as a trihalomethyl), and $R^{12}$ and $R^{17}$ are hydrogen; or if $R^8$ is a halogen, $R^{13}$ is a halogen, and $R^{12}$ and $R^{17}$ are hydrogen.

In all specific preferred compounds (I) in which (VI) and (VII) appear, it is preferred that $R^1$, $R^2$ and $R^3$ are hydrogen; and/or $R^4$ and $R^5$ are methyl. It is further preferred that:

$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group, more preferably methyl; or $R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group, more preferably ethyl; or $R^9$, $R^{10}$, $R^{11}$, $R^{12}$, $R^{14}$, $R^{15}$, $R^{16}$ and $R^{17}$ are all hydrogen; $R^{13}$ is isopropyl; and $R^8$ is a primary carbon group, more preferably isopropyl; or $R^9$, $R^{10}$, $R^{11}$, $R^{12}$, $R^{14}$, $R^{15}$, $R^{16}$ and $R^{17}$ are all hydrogen; $R^{13}$ is n-propyl; and $R^8$ is a primary carbon group, more preferably n-propyl; or $R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen, more preferably chloro; or $R^9$, $R^{10}$, $R^{11}$, $R^{12}$, $R^{14}$, $R^{15}$, $R^{16}$ and $R^{17}$ are all hydrogen; $R^{13}$ is trihalomethyl, more preferably trifluoromethyl; and $R^8$ is a trihalomethyl, more preferably trifluoromethyl.

In another preferred embodiment of (I), $R^6$ and $R^7$ are, respectively

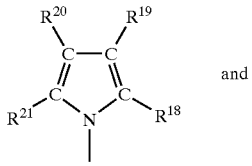

(VIII)

and

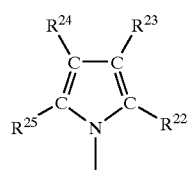

(IX)

wherein:

$R^{18}$ is a halogen, a primary carbon group, a secondary carbon group or a tertiary carbon group; and $R^{19}$, $R^{20}$, $R^{23}$ and $R^{24}$ are each independently hydrogen, hydrocarbyl, substituted hydrocarbyl or a functional group; Provided that:

when $R^{18}$ is a halogen or primary carbon group none, one or two of $R^{21}$, $R^{22}$ and $R^{25}$ are a halogen or a primary carbon group, with the remainder of $R^{21}$, $R^{22}$ and $R^{25}$ being hydrogen;

when $R^{18}$ is a secondary carbon group, none or one of $R^{21}$, $R^2$ and $R^{25}$ is a halogen, a primary carbon group or a secondary carbon group, with the remainder of $R^{21}$, $R^{22}$ and $R^{25}$ being hydrogen;

when $R^{18}$ is a tertiary carbon group, none or one of $R^{21}$, $R^{22}$ and $R^{25}$ is a tertiary carbon group, with the remainder of $R^{21}$, $R^{22}$ and $R^{25}$ being hydrogen;

and further provided that any two of $R^{18}$, $R^{19}$, $R^{20}$, $R^{21}$, $R^{22}$, $R^{23}$, $R^{24}$ and $R^{25}$ vicinal to one another, taken together may form a ring.

In the above formulas (VII) and (IX), $R^{18}$ corresponds to the second ring atom adjacent to the first ring atom bound to the imino nitrogen, and $R^{21}$, $r^{22}$ and $R^{25}$ correspond to the other ring atoms adjacent to the first ring atom.

In compounds (I) containing (VIII) and (IX), it is particularly preferred that if $R^{18}$ is a primary carbon group, $R^{22}$ is a primary carbon group, and $R^{21}$ and $R^{25}$ are hydrogen; or if $R^{18}$ is a secondary carbon group, $R^{22}$ is a primary carbon group or a secondary carbon group, more preferably a secondary carbon group, and $R^{21}$ and $R^{25}$ are hydrogen; or if $R^{18}$ is a tertiary carbon group (more preferably a trihalo tertiary carbon group such as a trihalomethyl), $R^{22}$ is a tertiary carbon group (more preferably a trihalotertiary group such as a trihalomethyl), and $R^{21}$ and $R^5$ are hydrogen; or if $R^{18}$ is a halogen, $R^{22}$ is a halogen, and $R^{21}$ and $R^{25}$ are hydrogen.

In all specific preferred compounds (I) in which (VIII) and (IX) appear, it is preferred that $R^1$, $R^2$ and $R^3$ are hydrogen; and/or $R^4$ and $R^5$ are methyl. It is further preferred that:

$R^{19}$, $R^{20}$, $R^{21}$, $R^{23}$ and $R^{24}$ are all hydrogen; $R^{22}$ is methyl; and $R^{18}$ is a primary carbon group, more preferably methyl; or $R^{19}$, $R^{20}$, $R^{21}$, $R^{23}$ and $R^{24}$ are all hydrogen; $R^{22}$ is ethyl; and $R^{18}$ is a primary carbon group, more preferably ethyl; or $R^{19}$, $R^{20}$, $R^{21}$, $R^{23}$ and $R^{24}$ are all hydrogen; $R^{22}$ is isopropyl; and $R^{18}$ is a primary carbon group, more preferably isopropyl; or $R^{19}$, $R^{20}$, $R^{21}$, $R^{23}$ and $R^{24}$ are all hydrogen; $R^{22}$ is n-propyl; and $R^{18}$ is a primary carbon group, more preferably n-propyl; or $R^{19}$, $R^{20}$, $R^{21}$, $R^{23}$ and $R^{24}$ are all hydrogen; $R^{22}$ is chloro or bromo;

and $R^{18}$ is a halogen, more preferably chloro or bromo.

The other type of ethylene olgimerization catalyst is typified by that described in U.S. Pat. No. 5,382,738. Typically these types of catalysts produce (predominantly) a single olefin having a relatively low number of carbon atoms, such as 1-hexene or 1-octene. These types of catalysts may also be used in the present processes to oligomerize ethylene as described in the references concerning these catalysts.

It is preferred that an ethylene oligomerization catalyst system that produces a homologous series of o-olefins be used. It is also preferred that this catalyst system produces a product with a high molar percentage (at least about 80 mole percent preferably at least about 90 mole percent) of olefins of the formula $H(CH_2CH_2)_n CH=CH_2$ (V), wherein n is 1 or more.

The production of the HTAC from an LTAC and the α-olefin(s) can be carried out by methods known in the art, see for instance U.S. Pat. Nos. 2,959,607, 3,180,881, 3,207,770, 3,389,161, 3,474,122,3,494,948, 4,918,254 and 5,278,330 and W. Gerhartz, et al., Ed., Ullmann's Encyclopedia of Industrial Chemistry, 5th Ed., Vol. A1, VCH Verlagsgesellschaft mbH, Weinheim, 1985, p. 545–549, both of which are hereby included by reference. Typical reaction temperatures are 80° C. to 150° C. for a period of about 1 hour to about 24 hours. In this reaction it is sometimes preferred to use an LTAC whose alkyl groups are branched, since these often are more reactive than LTACs having unbranched alkyl groups. It is believed that the reaction of the higher olefins with an LTAC is an equilibrium reaction, for example the reaction between TEA and 1-dodecene may be written as:

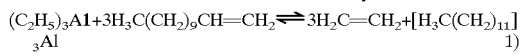
$(C_2H_5)_3Al+3H_3C(CH_2)_9CH=CH_2 \rightleftharpoons 3H_2C=CH_2+[H_3C(CH_2)_{11}]_3Al$  1)

During the reaction, which is run at, say, 100° C., the ethylene is usually volatilized, thereby driving the equilibrium to the right and resulting in (principally) tri-1-dodecylaluminum. Thus in these reaction it is preferred to run the reaction above the boiling point of the alkene which may be derived from the alkyl group of the LTAC. If olefins are present in the olefin mixture made during the oligomerization of ethylene which also have low boiling points, they too may be distilled.

This points out an interesting variation of this process which can be used to make a combination of lower α-olefins and higher α-alcohols. Lower α-olefin are desirable for use as comonomers, while it is often the α-alcohols which contain 10 or more carbon atoms which are desired. For example if one wanted to isolate octenes and lower molecular weight α-olefins from this process, one would use approximately only enough LTAC only to react with the total amount of α-olefins having 10 or more carbon atoms, and the reaction temperature would be controlled so that it would be above the boiling point of 1-octene (121° C. at atmospheric pressure), so as to distill off 1-octene and lower olefins, including the olefin formed from the LTAC. Conveniently this can be done by using a moderate amount of an inert solvent (see below), which preferably can be separated from the α-alcohols which will eventually be formed by distillation. In this instance a convenient solvent may be m-xylene (boiling point 139° C. at atmospheric pressure), much below the atmospheric boiling point of 1-decanol of 229° ° C. Thus the overall process may produce HTAC(s), α-alcohols, or a mixture of higher α-alcohols and (relatively) lower α-olefins.

It should be pointed out however that the reaction shown in equation 1 above is an ideal one, and other side reactions may take place. For example one or more of the alkyl groups on the aluminum may be a 2-dodecyl group instead of a 1-dodecyl group, or 1-dodecene may insert in an already formed C-Al bond of a 1-dodecyl group to give a branched $C_{24}$ alkyl group attached to aluminum. These are usually relatively minor reactions when the process is run at optimum conditions (temperature for instance). So it is possible that changing from the optimum temperature to make the desired HTAC to also isolate some lower α-olefins may cause the HTAC(s) isolated to have a somewhat different composition (more branching in the alkyl groups for example). These factors may be worked out by relatively simple experimentation.

Preferably the α-olefin(s) from the ethylene oligomerization reaction undergo little or no purification before being put into the process to make the HTAC If a mixture of α-olefins are produced they are preferably not separated. The ethylene oligomerization catalyst may be deactivated or not (if present it may be deactivated by the usually higher temperatures of the HTAC forming process). A solvent may be used in the ethylene oligomerization reaction, and preferably it does not contain active hydrogen compounds such as water, alcohols or carboxylic acids. If the solvent does not contain active hydrogen compounds it does not need to be separated before the reactions to form the HTAC. The solvent may also be added to the process in which the HTAC is formed. Preferred solvents in the oligomerization and/or HTAC forming reactions, if any, are nonolefinic hydrocarbons such as toluene, xylene, octane, cyclohexane, and the like. The composition of the HTAC(s) produced will depend on the composition of the α-olefin (mixture) added to the HTAC forming reaction, and as noted above the stoichiometry of the HTAC forming reaction and the temperature at which it is run.

Reaction of the HTAC(s) with oxygen or other oxidizing agent to form higher trialkoxyaluminum compounds can be carried out as known in the art, see for instance Elvers, et al., Ed., Ullmann's Encyclopedia of Industrial Chemistry, 5th Ed., Vol. A28, VCH Verlagsgesellschaft mbH, Weinheim, 1996, p. 505–508 and references therein, and U.S. Pat. No. 5,278,330 which is hereby included by reference. Likewise, the hydrolysis of the higher trialkoxyaluminum compound to form α-alcohols may be carried out by methods known in the literature, see for instance Elvers, et al., Ed., Ullmann's Encyclopedia of Industrial Chemistry, 5th Ed., Vol. A28, VCH Verlagsgesellschaft mbH, Weinheim, 1996, p. 505–508 and references therein. These methods for oxidation and hydrolysis to form α-alcohols are known in the art.

The present process form making the HTAC(s) and/or α-alcohols result in less handling of pyrophoric alkylaluminum compounds at high temperatures and/or pressure, thereby making the process safer and/or lowering operating cost, and/or lowering investment need for the plant, when compared to the conventional methods of manufacturing these types of compounds. Assuming a mixture of homologous α-olefins is used to make the HTAC, the product mixture resulting, for example, from making α-alcohols may be similar to that obtained with current manufacturing methods.

The α-alcohols and α-olefins (from the reaction forming the HTAC) produced may be fully or completely purified (separated) by distillation, as is known in the art.

What is claimed is:

1. A process for the manufacture of higher trialkylaluminum compounds, comprising, forming an α-olefin or mixture of α-olefins by oligomerization of ethylene using a transition metal containing oligomerization catalyst system, then contacting said α-olefin or said mixture of α-olefins with a lower trialkylaluminum compound at a sufficient temperature, for a sufficient amount of time, to form a higher trialkylaluminum compound.

2. A process for the manufacture of α-alcohols, comprising:

(1) forming an α-olefin or mixture of α-olefins by oligomerization of ethylene using a transition metal containing oligomerization catalyst system;

(2) contacting said α-olefin or said mixture of α-olefins with a lower trialkylaluminum compound at a sufficient temperature, for a sufficient amount of time, to form a higher trialkylaluminum compound or a mixture thereof;

(3) contacting said higher trialkylaluminum compound or a mixture thereof with oxygen or other suitable oxidizing agent to form a higher trialkoxyaluminum compound or a mixture thereof; and (4) hydrolyzing said higher trialkoxyaluminum compound or a mixture thereof to form an α-alcohol or a mixture thereof.

3. The process as recited in claim 1 or 2 wherein said mixture of olefins is used and is a homologous series of α-olefins.

4. The process as recited in claim 1 or 2 wherein said homologous series of α-olefins is produced in an oligomerization reaction which has a Schulz-Flory constant of about 0.6 to about 0.8.

5. The process as recited in claim 1, 2, 3 or 4 wherein said transition metal containing oligomerization catalyst system comprises an iron complex of a diimine of a 2,6-diacylpyridine or a 2,6-pyridinedicarboxaldehyde.

6. The process as recited in claim 5 wherein said iron complex is a compound of the formula

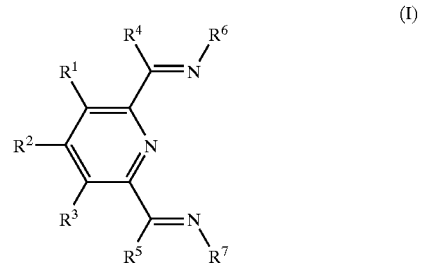

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

7. The process as recited in claim 1 or 2 wherein a single α-olefin is used.

* * * * *